United States Patent [19] [11] 3,954,439
Papamichael et al. [45] May 4, 1976

[54] HERBICIDAL COMPOSITIONS
[75] Inventors: Stavros Papamichael, Cambridge; Ross Mortimore Ward Dyer, Cheadle, both of England
[73] Assignee: Ciba-Geigy Corporation, Ardsley, N.Y.
[22] Filed: Mar. 8, 1973
[21] Appl. No.: 339,063

[30] Foreign Application Priority Data
Aug. 3, 1972   United Kingdom............... 10751/72
Jan. 24, 1973   United Kingdom................. 3607/73

[52] U.S. Cl......................................... 71/93; 71/88; 71/92; 71/117; 71/119; 71/120; 71/121; 71/DIG. 1
[51] Int. Cl.²........................................... A01N 9/22
[58] Field of Search.............. 71/79, DIG. 1, 93, 88, 71/119, 120, 121

[56] References Cited
UNITED STATES PATENTS
2,992,090   7/1961   Littler..................................... 71/93
3,657,446   4/1972   Blackmore........................ 71/DIG. 1
3,737,551   6/1973   Karsten et al..................... 71/DIG. 1
3,791,811   2/1974   French.............................. 71/DIG. 1

*Primary Examiner*—Glennon H. Hollrah
*Attorney, Agent, or Firm*—Harry Falber; Karl F. Jorda

[57] ABSTRACT

The invention relates to herbicidal compositions in granular form comprising a herbicidal material and at least 5% by weight, preferably 5% to 15% by weight, based on total solids of one or more surfactants.

23 Claims, No Drawings

HERBICIDAL COMPOSITIONS

The present invention relates to granular compositions comprising a herbicidal agent and one or more surfactants and processes for the production of such compositions.

There is a need in many fields of activity for processes whereby active ingredients can be evenly distributed over an area or throughout a volume. If the dosage rate is high, then conventional distribution techniques can be used; if the rate is to be low, however, the only really simple and foolproof method involves diluting the active ingredient with an inert diluent, and then dispersing the diluted mixture. Usual diluents are water, inexpensive solvents, inert powders and granular carriers, the choice of diluent being determined primarily by the physical and chemical characteristics of the active ingredient and the equipment available.

Many active ingredients to be distributed at low dosage rates are in fact powders which are substantially insoluble in water or common solvents. Where distribution in liquid form, for example by spraying, is desirable, the active ingredient is often formulated as a wettable powder which can subsequently be dispersed into a suitable liquid carrier to form a stable or at least semi-stable dispersion suitable for such distribution. Wettable powders are normally prepared by mixing all the ingredients of the formulation in a blender, and then milling with further mixing as necessary to obtain homogeneity as far as possible. Such powders have drawbacks; for example they are often dusty, and this is highly undesirable if the active ingredient is toxic or irritating to human beings.

Additionally, wettable powders frequently require to be pre-creamed, that is to say they must be mixed with a small amount of liquid dispersant to form a homogeneous paste free from lumps before they can be diluted to the desired final concentration for use.

One class of active material which has always involved difficulties of distribution is that of the substantially insoluble herbicides used in agriculture and horticulture. These have usually been supplied to date as wettable powders, with the attendant drawbacks already listed, pastes or suspension concentrates.

The latter two are in general less popular and satisfactory alternatives to the wettable powders either because of relatively high manufacturing costs, inconvenience in handling, packing and storage or inferior physical characteristics, for instance, stability and ease of dispersion.

A herbicide composition designed for dispersion in a liquid carrier should ideally have a high content of active material, should be readily dispersible in the carrier and should then form a dispersion which is as stable as possible, requiring the minimum of subsequent agitation for homogeneity The liquid carrier will, of course, for convenience normally be water. We have now devised a way of making such insoluble powdered active ingredients into granules which readily break down when they are stirred into a liquid carrier to give a stable dispersion of the active ingredient.

According to this invention, there is provided a composition, in granular form, comprising a herbicidal material and at least 5% by weight, based on total solids of one or more surfactants.

By granular form, we mean granules at least substantially all of which have a mean particle size of at least 0.1 mm, i.e. a particle size much larger than the mean particle size of a powder, the mean particle size of which is measured in microns.

Preferably, the composition contains at least 50%, more preferably at least 80% of the herbicidal material and the total composition preferably has an active suspensibility (according to the W.H.O. Suspensibility Test) of at least 60%, when measured as a 0.9% to 2.0% weight/volume dispersion in W.H.O. standard hard water.

The composition of this invention can be prepared for instance by mixing a solution, preferably an aqueous solution, containing one or more surfactants with the herbicidal material, with or without carrier, in powder form to give a paste or slurry in which the solid material is uniformly distributed in the liquid medium. Some of the solvent may have to be removed depending on the subsequent granulation method to be employed, and the residue converted into granular form by any suitable technique. For example, the paste can be dried by such known techniques as spray drying, freeze drying or drying in a fluid bed. More conveniently, the paste is dried in an oven, desirably one equipped with means for removing the solvent vapour, prior to extruding and drying the granules in the oven. Alternatively, the paste can be completely dried and then broken up by any suitable granulation method.

By preparing the granular herbicidal composition in this way, a product is obtained which is non-dusting and which is readily dispersible in water without the necessity for pre-creaming.

An added advantage of this process is that we can combine insoluble active herbicide ingredients and soluble active ingredients in our dispersible granules. A soluble ingredient in an aqueous solution of its own, or in an aqueous solution of a surfactant, may be incorported into the homogeneous paste or slurry before the latter is granulated.

A preferred process of producing a granular herbicidal composition according to the present invention comprises a. milling the herbicide or mixture of herbicides until they are in a state of fine particles size distribution, preferably from 10 – 30 microns with at most only a few percent of the particles being larger than 44 microns in diameter.

b. dissolving the surfactant, preferably a mixture of a dispersing agent and a wetting agent, in a predetermined amount of water so that after step (c) an extrudable paste is obtained.

c. Slowly adding the solution of the surfactant to the herbicide, with or without carrier, in a high-shear mixer, for instance a kneading machine, and mixing thoroughly until a homogeneous extrudable paste is obtained; alternatively, the milled herbicide or mixture of herbicides, with or without carrier, is added slowly to the solution of the surfactant.

d. extruding the paste obtained in step (c)

e. drying the extruded granules and sieving them to remove any undersize material, i.e. dust-like "fines".

In step (a), the milling is preferably continued until less than 1% of residue remains on a 44 micron sieve when the material in the mill is subjected to wet sieve analysis.

The preferred process of the present invention is particularly advantageous in that the water used in the formation of the paste, does not need to be removed prior to granulation in a separate process step, so that valuable time and expense are saved.

The process according to the invention is applicable to those herbicides which are substantially insoluble in water, by which we include the chlorotriazines, methylthiotriazines, substituted ureas, azidotriazines, mixtures of chlorotriazines with methylthiotriazines and mixtures of triazines with water-soluble herbicides and other water insoluble herbicides. All these products may be described as comprising one or more substantially water-insoluble herbicides or a substantially water-insoluble herbicide and a water-soluble one. Particular success has been obtained with simazine, atrazine, terbuthylazine, terbutryne, aziprotryne, chloroxuron, fluometuron, chlortoluron, prometryne, desmetryne, ametryne, a mixture of terbuthylazine and terbutryne, a mixture of atrazine, aminotriazole and 2,4-dichlorophenoxyacetic acid, a mixture of simazine and aminotriazole and a mixture of bromofenoxim and triazines.

In the case of bromofenoxim compositions, the preferred granular compositions according to the invention include, as herbicidal material, a mixture selected from a. Bromofenoxim and Terbuthylazine
b. Bromofenoxim and Atrazine
c. Bromofenoxim, Terbuthylazine and Atrazine The compound "Bromofenoxim" is 3,5-dibromo-4-hydroxy-benzaldoxime-0-(2',4'-dinitrophenyl) ether, "Terbuthylazine" is 2-chloro-4-ethylamino-6-tert. butylamino-s-triazine and "Atrazine" is 2-chloro-4-ethylamino-6-isopropylamino-s-triazine.

For mixture (a), the preferred weight ratio of Bromofenoxim to Terbuthylazine is from 10 : 1 to 1 : 3. For mixture (b) the preferred weight ratio of Bromofenoxim to Atrazine is from 20 : 1 to 1 : 2.

In the case of mixture (c), preferably the weight ratio of Bromofenoxim to the total of Atrazine + Terbuthylazine is from 10 : 1 to 1 : 3, and the preferred weight ratio of Atrazine to Terbuthylazine in mixture (c) is from 1 : 5 to 10 : 1.

It is obviously desirable that the granules should have the highest possible content of active herbicidal material. While the process according to the invention is preferably carried out so as to give granules containing at least 50% of active herbicide material, it is more preferable that the granules should contain more than this, that is at least 80% and even up to 95%. In some cases however, it is necessary to include a proportion of a carrier such as china clay, chalk or a silicate so that the active ingredient will not then greatly exceed 80% of the granules.

One of the preferred properties of the granules prepared according to the invention is that their active suspensibility is at least 60% when measured as a 0.9% or higher (depending on the conc. of the active ingredient) w/v suspension in W.H.O. standard hard water. More preferably however the active suspensibility should be at least 75%.

It is desirable that the particle size of the powdered active herbicide ingredient to be used in the process according to the invention should not exceed 100 microns, and should preferably be even less, not exceeding 44 microns. The larger the particles, the faster they will tend to settle out from suspension, and particles above 100 microns may block filters or roses of spraying apparatus. We prefer that the particle size should be from 10 – 30 microns, with at most a few percent of particles larger then 44 microns in diameter.

Any suitable surfactant or mixture of surfactants may be used. Preferably anionic or non-ionic surfactants or mixtures of the two are employed. The preferred way of carrying out the process is to use one surfactant which can function as a wetting agent, and a surfactant which can function as a dispersing agent, although these two classes can overlap to a considerable extent. Ethylene oxide condensates, for example of alkyl phenols or fatty alcohols, are examples of surfactants which function as wetting agents, and lignosulphonates and ammonium salts of mixtures of aromatic sulphone sulphonic acids condensed with formaldehyde are examples of surfactants which act as dispersing agents.

The relative proportions of wetting agent to dispersing agent are important if optimal distribution of herbicide in the final dispersion is to be achieved. Moreover, in order to obtain a herbicidal composition with the maximal proportion of active ingredient, it is obviously important to keep the total surfactant content down to the minimum. In this connection, it is essential to use at least 5% of total surfactant; preferably the total surfactant content is from 5 to 15%, based on total weight of the formulation.

In the preferred instance, in which the surfactant used consists of a mixture of a dispersing agent and a wetting agent, the relative ratio of dispersing agent to wetting agent is advantageously at least 2 to 1, preferably at least 4 to 1, by weight.

Another practical advantage of the herbicidal compositions of this invention which desirably contain from 80% to 95% by weight of active ingredient is a reduction in the quantity of material to be handled with consequent savings in handling, packaging and transportation costs.

Some Examples will now be given:

EXAMPLE 1

A solution of 2g. of the condensate of nonylphenol with 9/10 moles of ethylene oxide and 8g. of the ammonium salt of a mixture of aromatic sulphone sulphonic acids condensed with formaldehyde in 70 ml. of water was added to 90g. of simazine technical (3% of particles greater than $44\mu$) in a beaker. The resulting suspension was stirred vigorously until a homogeneous paste was formed and then dried with occasional stirring in a fan blown oven at 50–60° C. The dried cake thus obtained was then broken down to the required particle size (0.8–2.0 mm.). Using normal packing procedures, these granules were found to have a bulk density of about 0.36 Kg/l. The granules were found to disperse readily in water to give a stable suspension on stirring. The active suspensibility of a 1.0% w/v dispersion in W.H.O. standard hard water was found to be 78–79%.

EXAMPLE 2

A solution of 2g. of the nonyl phenol/ethylene oxide condensate and 8g. of the ammonium salt, each used in Example 1, in 70 ml. of water was added to 90g. of milled simazine technical (0.5% of particles greater than $44\mu$) in a beaker. The resulting suspension was stirred vigorously until a homogeneous paste was formed and then dried with occasional stirring in a fan blown oven at 50° – 60° C. The dried cake thus obtained was then broken down to the required particle size (0.8–2.0 mm.). The granules thus obtained were found to disperse readily in water to give a stable suspension on stirring. The active suspensibility of a 1.0% w/v dispersion in W.H.O. standard hard water (342 ppm. calculated as calcium carbonate) was found to be 90–92%.

This example illustrates the superior suspensibility obtained when starting with milled active ingredient essentially all of which has a particle size below 44$\mu$.

EXAMPLE 3

A solution of 1g. of the nonyl phenol/ethylene oxide condensate and 4g. of the ammonium salt, each used in Example 1, in 70 ml. of water was added to 95g. of simazine technical in a beaker. The resulting suspension was stirred vigorously until a homogeneous paste was formed, and some of the water was then evaporated off in a fan-blown oven at 50 – 60° C. The resulting thick paste was granulated by extrusion. The granules thus obtained were found to disperse readily in water to give a stable suspension on stirring. The active suspensibility of a 1.0% w/v dispersion in W.H.O. standard hard water (342 ppm. calculated as calcium carbonate) was found to be 75 – 78%.

EXAMPLE 4

The procedure described in Example 1 was repeated except that the simazine technical was replaced by atrazine technical (of similar particle size). The granules obtained were found to disperse readily in water to give a stable suspension on stirring. The active suspensibility of a 1.0% dispersion in W.H.O. standard hard water (342 ppm. calculated as calcium carbonate) was found to be 75 – 80%.

EXAMPLE 5

The procedure described in Example 2 was repeated except that the milled technical simazine was replaced by milled technical atrazine (of similar particle size). The granules obtained were found to disperse readily in water to give a stable suspension on stirring. The active suspensibility of a 1.0% w/v dispersion in W.H.O. standard hard water (342 ppm. calculated as calcium carbonate) was found to be 85 – 90%.

EXAMPLE 6

The procedure described in Example 3 was repeated except that the simazine technical was replaced by atrazine technical. The granules obtained were found to disperse readily in water to give a stable suspension on stirring. The active suspensibility of a 1.0% dispersion in W.H.O. standard hard water (342 ppm. calculated as calcium carbonate) was found to be 75–80%.

EXAMPLE 7

50 parts of Bromofenoxim and 30 parts of Terbuthylazine in the form of the technical materials were milled until the mill charge left less than 1% residue on a 44 micron sieve when the charge was subjected to wet sieve analysis.

12 parts of a dispersing agent consisting of the ammonium salt of a mixture of aromatic sulphone sulphonic acids condensed with formaldehyde and 3 parts of a wetting agent consisting of nonyl phenol condensed with 14 moles of ethylene oxide were dissolved in 25 parts of water.

The aqueous solution of the surfactants was added slowly to the herbicide and inert carrier (approx 5 parts of sodium aluminum silicate) mixture in a kneader until a homogeneous extrudable paste was obtained. Alternatively, the milled herbicides and the inert carrier can be added slowly to the solution of the surfactants in a kneader and mixed until a homogeneous extrudable paste is obtained.

The paste so obtained was then extruded and the extruded granules were dried and sieved to remove fines. The active suspensibility of a 1.0% dispersion in W.H.O. standard hard water (342 ppm calculated as $CaCO_3$) was 78–80%.

EXAMPLE 8

Using the procedure described in Example 7, granules were prepared from the following starting materials:

37.5 parts of Bromofenoxim in the form of the technical material
22.5 parts of Terbuthylazine technical
12.0 parts of the ammonium salt of a mixture of aromatic sulphone sulphonic acids condensed with formaldehyde
3.0 parts of a nonyl phenol/ethylene oxide condensate (14 moles of ethylene oxide)
Rest china clay.
The active suspensibility of a 2.0% dispersion in W.H.O. standard hard water (342 ppm calculated as $CaCO_3$) was 75–78%.

EXAMPLE 9

Using the procedure described in Example 7, granules were prepared from the following starting materials:

60 parts of Bromofenoxim in the form of the technical material
20 parts of Atrazine in the form of the technical material
12 parts of the ammonium salt of a mixture of aromatic sulphone sulphonic acids condensed with formaldehyde
3 parts of a nonyl phenol/ethylene oxide condensate (14 moles of ethylene oxide)
Rest sodium aluminium silicate
The active suspensibility of a 1.0% dispersion in W.H.O. standard hard water (342 ppm calculated as $CaCO_3$) was 84–85%.

EXAMPLE 10

Using the procedure described in Example 7, granules were prepared from the following starting materials:

90 parts of simazine technical
7 parts of the ammonium salt of a mixture of aromatic sulphone sulphonic acids condensed with formaldehyde
3 parts of nonyl phenol/ethylene oxide condensate (9/10 moles of ethylene oxide)
The granules obtained had an active suspensibility as a 1.0% dispersion in W.H.O. standard hard water (342 ppm calculated as $CaCO_3$) of 88–90%.

EXAMPLE 11

Using the procedure described in Example 7, granules were prepared from the following starting-materials:

80 parts of Atrazine in the form of technical material
12 parts of the ammonium salt of a mixture of aromatic sulphone sulphonic acids condensed with formaldehyde 3 parts of a nonyl phenol/ethylene oxide condensate (14 moles of ethylene oxide)
Rest china clay The granules had an active suspensibility of 88–90% as a 1.0% dispersion in W.H.O. standard hard water (342 ppm calculated as $CaCO_3$).

EXAMPLE 12

Using the procedure described in Example 7, granules were produced from the following starting-materials:
80 parts of desmetryne in the form of technical material
12 parts of the ammonium salt of a mixture of aromatic sulphone sulphonic acids condensed with formaldehyde
3 parts of a nonyl phenol/ethylene oxide condensate (14 moles of ethylene oxide)
Rest sodium aluminium silicate The granules obtained had an active suspensibility of 77–80% as a 1.0% dispersion in W.H.O. standard hard water (346 ppm calculated as $CaCO_3$).

EXAMPLE 13

Using the procedure described in Example 7, granules were prepared from the following starting-materials:
90 parts of chlortoluron technical
8 parts of the ammonium salt of a mixture of aromatic sulphone sulphonic acids condensed with formaldehyde
2 parts of a nonyl phenol/ethylene oxide condensate (9 to 10 moles of ethylene oxide)

The granules obtained had an active suspensibility of 70% as a 1.0% dispersion in W.H.O. standard hard water (342 ppm calculated as $CaCO_3$).

We claim:

1. A composition, in water dispersable granular form, comprising at least 50% by weight, based on total solids, of a herbicidal material selected from the group consisting of chlorotriazines, methylthiotriazines, substituted ureas, azidotriazines, 3,5-dibromo-4-hydroxy-benzaldoxime-0-(2',4'-dinitrophenyl)ether, and mixtures thereof and from about 5–15% by weight, based on total solids, of one or more surfactants selected from the group consisting of ethylene oxide condensates with alkyl phenols or fatty alcohols, lignosulphonates, ammonium salts of mixtures of aromatic sulphone sulphonic acids condensed with formaldehyde, and mixtures thereof; substantially all of said granules having a mean particle size of at least 0.1 mm; said composition having an active suspensibility, as hereinbefore defined, of at least 60%.

2. A composition as claimed in claim 1 wherein the composition contains at least 80% of the herbicidal material.

3. A composition as claimed in claim 1 wherein the total composition has an active suspensibility of at least 75%.

4. A composition as claimed in claim 1 wherein the herbicidal material is a mixture of a water-insoluble herbicide with a water-soluble herbicide.

5. A composition as claimed in claim 4 wherein the water-insoluble herbicide is a triazine or a substituted urea.

6. A composition as claimed in claim 1 wherein a mixture of surfactants is used one of which can function as a wetting agent and the other as a dispersing agent.

7. A composition as claimed in claim 6, wherein the wetting agent is an alkyl phenol or fatty alcohol condensate of ethylene oxide.

8. A composition as claimed in claim 6, wherein the dispersing agent is a lignosulphonate or an ammonium salt of an aromatic sulphone sulphonic acid condensate with formaldehyde.

9. A composition as claimed in claim 6 wherein the relative ratio of dispersing agent to wetting agent is at least 2:1 by weight.

10. A composition as claimed in claim 9, wherein the relative ratio of dispersing agent to wetting agent is at least 4:1 by weight.

11. A composition as claimed in claim 1 wherein a carrier is present.

12. A composition as claimed in claim 11 wherein the carrier is china clay, a silicate or chalk.

13. A process of producing a composition as defined in claim 1 comprising mixing an aqueous solution containing from about 5–15% by weight, based on total solids, of one or more surfactants selected from the group consisting of ethylene oxide condensates with alkyl phenols or fatty alcohols, lignosulphonates, ammonium salts of mixtures of aromatic sulphone sulphonic acids condensed with formaldehyde, and mixtures thereof with at least 50% by weight, based on total solids, of a herbicidal material selected from the group consisting of chlorotriazines, methylthiotriazines, substituted ureas, azidotriazines, 3,5-dibromo-4-hydroxy-benzaldoxime-0-(2',4'-dinitrophenyl) and mixtures thereof, with or without carrier, in powder form so that a paste or slurry in which the solid material is uniformly distributed in the liquid medium is formed, optionally removing some of the water and then converting the residue into granular form having a mean particle size of at least 0.1 mm.

14. A process as claimed in claim 13, wherein the paste dried in an oven, prior to being extruded.

15. A process as claimed in claim 13 wherein the paste is completely dried and then broken up into granules.

16. A process as claimed in claim 13 wherein the particle size of the powdered herbicidal material does not exceed 44 microns.

17. A process as claimed in claim 16 wherein the particle size of the powdered herbicidal material is from 10 30 microns.

18. A composition, in water dispersable granular form, comprising from about 5–15% by weight, based on total solids, of one or more surfactants and, as herbicidal material, at least 50% by weight, based on total solids, of a mixture selected from a. 3,5-dibromo-4-hydroxy-benzaldoxime-0-(2',4'-dinitrophenyl)ether and 2-tert.butylamino-4-chloro-6-ethylamino-s-triazine;

b. 3,5-dibromo-4-hydroxy-benzaldoxime-0-(2',4'-dinitrophenyl)ether and 2-chloro-4-ethylamino-6-isopropylamino-s-triazine; and, c. 3,5-dibromo-4-hydroxy-benzaldoxime-0-(2',4'-dinitrophenyl)ether, 2-tert.butylamino-4-chloro-6-ethylamino-s-triazine and 2-chloro-4-ethylamino-6-isopropylamino-s-triazine.

19. A composition as claimed in claim 18 wherein, in mixture (a), the weight ratio of oxime to triazine is from 10:1 to 1:3; in mixture (b), the weight ratio of oxime to triazine is from 20:1 to 1:2; and in mixture (c)

the weight ratio of oxime to total triazine is from 10:1 to 1:3 and the weight ratio of 2-chloro-triazine to 4-chlorotriazine is from 1:5 to 10:1.

20. A process of producing a granular, water dispersable herbicidal composition comprising
   a. milling at least 50% by weight, based on total solids of a herbicide selected from the group consisting of chlorotriazines, methylthiotriazines, substituted ureas, azidotriazines, 3,5-dibromo-4-hydroxy-benzaldoxime-0-2',40'-dinitrophenyl)ether, and mixtures thereof until it is in a state of fine particle size distribution,
   b. dissolving from about 5–15% by weight, based on total solids, of a surfactant selected from the group consisting of ethylene oxide condensates with alkyl phenols or fatty alcohols, lignosulphonates, ammonium salts of mixtures of aromatic sulphone sulphonic acids condensed with formaldehyde, and mixtures thereof in a pre-determined amount of water so that after step (c) an extrudable paste is obtained,
   c. slowly adding the surfactant solution to the herbicide, with or without a carrier in a high-shear mixer and mixing thoroughly until a homogeneous extrudable paste is obtained; alternatively the milled herbicide or mixture or herbicides, with or without carrier, is added slowly to the solution of the surfactant,
   d. extruding the paste obtained in step (c), and
   e. drying the extruded granules and removing any material having a mean particle size less than about 0.1 mm.; said composition having an active suspensibility of at least 60%.

21. A process as claimed in claim 20, wherein the milling in step (a) is continued until the herbicide particle size distribution is from 10 – 30 microns with less than 1% of the particles being larger than 44 microns in diameter.

22. A process as claimed in claim 21, wherein the surfactant in step (b) is a mixture of a dispersing agent and a wetting agent.

23. A process as claimed in claim 21, wherein the high-shear mixer is a kneading machine.

* * * * *